United States Patent [19]
Penton et al.

[11] Patent Number: 4,592,755
[45] Date of Patent: Jun. 3, 1986

[54] MAMMARY IMPLANT

[75] Inventors: Harold R. Penton; Michael E. Kucsma; F. Alexander Pettigrew, all of Baton Rouge, La.

[73] Assignee: Ethyl Corporation, Richmond, Va.

[21] Appl. No.: 743,524

[22] Filed: Jun. 11, 1985

[51] Int. Cl.⁴ .............................................. A61F 1/24
[52] U.S. Cl. ..................................... 623/8; 128/462; 128/DIG. 21
[58] Field of Search ............ 623/8; 128/462, DIG. 21

[56] References Cited

U.S. PATENT DOCUMENTS

| | | |
|---|---|---|
| 3,020,260 | 2/1962 | Nelson . |
| 3,293,663 | 12/1966 | Cronin . |
| 3,559,214 | 2/1971 | Pangman ................................. 623/8 |
| 3,665,520 | 5/1972 | Perras et al. . |
| 3,683,424 | 8/1972 | Pangman ................................. 623/8 |
| 3,986,213 | 10/1976 | Lynch ..................................... 623/8 |
| 4,100,627 | 7/1978 | Brill, III . |
| 4,205,401 | 6/1980 | Frisch . |
| 4,428,082 | 1/1984 | Naficy . |
| 4,455,691 | 6/1984 | Van Aken Redinger et al. . |

Primary Examiner—Gregory E. McNeill
Attorney, Agent, or Firm—Donald L. Johnson; John F. Sieberth; Joseph D. Odenweller

[57] ABSTRACT

A prosthesis for subcutaneous implantation such as a mammary implant used in reconstructive surgery is made from a polyphosphazene elastomer (e.g. polyfluoroalkoxy phosphazene) sac containing a silicone gel. The sac is essentially impermeable to the silicone gel fill and overcomes a gel migration problem encountered with implants made using polysiloxane sacs.

34 Claims, 2 Drawing Figures

MAMMARY IMPLANT

BACKGROUND OF THE INVENTION

Use of body implants in reconstructive surgery following mastectomy has been practiced for some time with a high rate of patient satisfaction. Early implants were made of a spongy material such as polyurethane which left much to be desired. Present day implants are generally made from a polysilicone elastomer sac filled with a silicone gel or mixture of silicone gel and silicone fluid. The first successful implant of such a prosthesis is credited to T. D. Cronin (Cronin, U.S. Pat. No. 3,293,663). Cronin's implant comprised a flexible sac made from silicone rubber with a silicone gel fill as described in U.S. Pat. No. 3,020,260. A polyester fabric was attached to the back of the sac which was invaded by tissue thus attaching the prosthesis to the chest wall.

Colette et al. U.S. Pat. No. 3,665,520 describes a similar prosthesis with an elongated tab extending toward the axilla region. A polyester felt is placed only along the edge of the tab for attachment to the chest wall. This sac was made of an organopolysiloxane polycarbonate block copolymer and filled with a silicone gel.

Lynch U.S. Pat. No. 3,883,902 describes a unitary sterile assembly including an empty silicone rubber sac attached to a reservoir for filling the sac with silicone gel after implantation.

Brill U.S. Pat. No. 4,100,627 recognized the problem of silicone gel migration in previous silicone gel-filled prosthetic devices. Brill used a conventional polydimethylsiloxane sac but substituted a cross-linked polydimethylsiloxane gel which is said to reduce leakage. However, since cross-linking is not 100% efficient, some un-crosslinked oil remains which will continue to leak. The polydimethylsiloxane elastomer used to make the sac can also contain other siloxane units such as methylvinylsiloxane, methylphenylsiloxane, diphenylsiloxane and 3,3,3-trifluoropropylsiloxane and can be end-blocked with conventional units such as dimethylvinylsiloxy, trimethylsiloxy or methylphenylvinylsiloxy units. The silicone rubber contains fillers such as silica, processing aids, additives, pigments and can be vulcanized or cured with organic peroxides or by irradiation.

Frisch U.S. Pat. No. 4,205,401 describes a mammary implant constructed to resist the effects of fibrous capsular contracture which tends to distort an implant into a spherical shape surrounded by a stiff fibrous capsule. Frisch lists various materials said to be useful in making the sac. These are cellulose acetate, cellulose acetate butyrate, cellulose nitrate, crosslinked polyvinyl alcohol, polyurethanes, nylon 6, nylon 66, aromatic nylon, polyvinyl acetate, plasticized polyvinyl acetate, polyvinyl butyrate, ethylene vinyl acetate copolymer, polyethylene, polypropylene, polyisobutylene, polyvinylchloride, plasticized polyvinylchloride, natural rubber, and synthetic elastomers such as silicone rubber and polybutadiene. Except for silicone rubber the list appears to be highly speculative. Frisch also discusses the technique of making the implant sac by dip coating a shaped mandrel, curing the sac on the mandrel and removing the sac from the mandrel.

Redinger et al. U.S. Pat. No. 4,455,691 notes the belief on the part of many surgeons that the reduction of silicone gel and oil migration from implants would be a definite improvement in reducing the problem of fibrous contraction which is said to occur in up to 40% of patients after implant (Baker et al. "Bleeding of Silicone From Bag-Gel Breast Implants and Its Clinical Relation to Fibrous Capsule Reaction", *Plastic and Reconstructive Surgery*, June 1976, Vol. 61, No. 6; Hausner et al. "Foreign-Body Reaction to Silicone Gel in Axillary Lymph Nodes After an Augmentation Mammaplasty", *Plastic and Reconstructive Surgery*, Sept. 1978, Vol. 62, No. 3). Redinger et al. impedes the migration of gel and oil through the sac walls by using a sac wall made of the reaction product of polydimethylsiloxane and either 3,3,3-trifluoropropylpolysiloxane, diphenylpolysiloxane or methylphenylpolysiloxane. Multi-layer sacs are disclosed wherein one of the layers is the barrier film. Methods for making these multi-layer implant sacs are discussed in detail.

SUMMARY OF THE INVENTION

It has now been discovered that implant sacs that are substantially impermeable to silicone gels and fluids can be made from cured polyphosphazene elastomers. In tests a lightly filled peroxide-cured polyfluoroalkoxy phosphazene elastomer exhibited bleed rates below the limit of detection in a standard test used in industry to measure membrane permeability.

DESCRIPTION OF THE PREFERRED EMBODIMENTS

Figure 1:
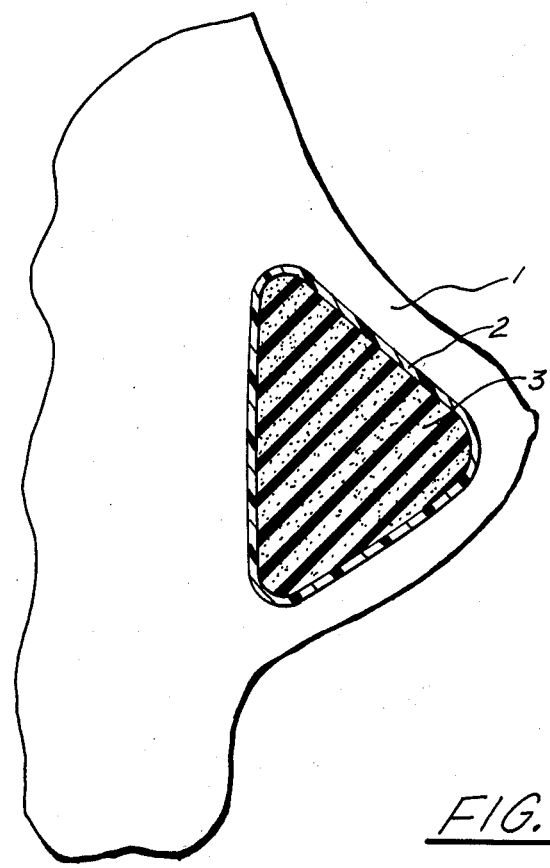
FIG. 1 is a cross-section of a human breast showing an implanted silicone gel-filled mammary prosthesis in place.
Figure 2:
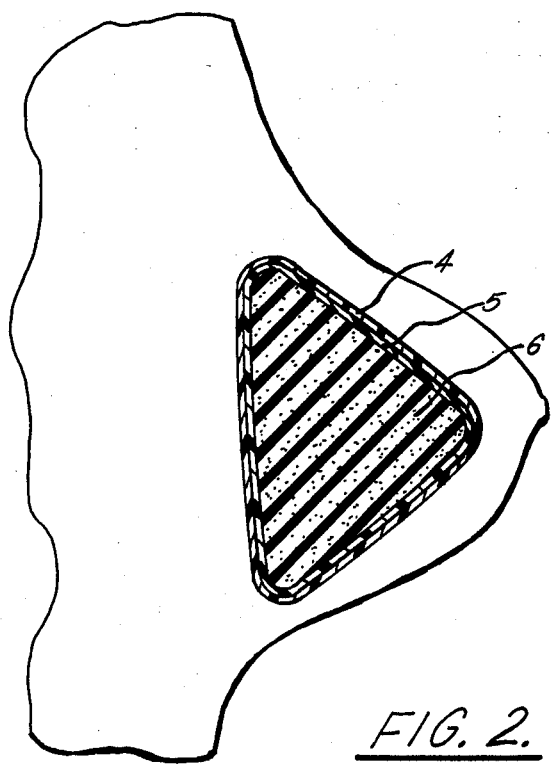
FIG. 2 is a cross-section similar to FIG. 1 but showing a two-layer sac which contains the silicone gel fill.

A preferred embodiment of the invention is an article of manufacture suitable for use as a body implant said article comprising a supple liquid-impermeable sac defining a cavity, said cavity containing an inert stable liquid, said sac comprising a continuous film of a cured polyphosphazene elastomer composition.

A further embodiment of the invention is a prosthesis for subcutaneous implantation in a patient having need for such implantation, said prosthesis comprising a leak-proof flexible sac containing a polysiloxane gel and/or oil, said sac comprising a continuous cured polyfluoroalkoxy substituted phosphazene elastomer wall which is substantially impermeable to said polysiloxane gel or oil. In a still further embodiment of the invention the prosthetic implant is constructed such that the wall is a two-layer wall, the inner layer in contact with the silicone gel comprising a cured polyfluoroalkoxy substituted phosphazene elastomer and the outer layer comprising a cured polysiloxane elastomer.

The implant sac may be constructed of a blend or alloy of a polyphosphazene elastomer with one or more different elastomers that form a compatible blend. These different elastomers include polysiloxanes (e.g. polydimethylsiloxane, polydiphenylsiloxane, polymethylphenylsiloxane, and the like), polyurethanes, polyesters, polyamides, polymethacrylates, styrenemaleic anhydride copolymer, polyphenylene ethers, poly(trifluoropropylsilicone). For example a polyphosphazenepolysiloxane blend could combine the silicone impermeability of the polyphosphazene with the excellent elongation of the silicone rubber.

The construction of the breast implants is well known and can be readily understood by reference to the drawings. In its simplest form, the implant comprises sac 1 constructed of a continuous membrane 2 forming a cavity which is filled with an inert stable liquid 3. In another embodiment the implant is a multilayer sac having an outer layer made of a polysiloxane film 4 and in an inner layer made of a polyphosphazene film 5 and is filled with a silicone oil and/or gel 6. The outer polysiloxane film functions to make the implant at least as body-compatible as present day silicone rubber sac implants and the inner polyphosphazene film acts as a barrier to prevent migration of the silicone oil or gel into the surrounding body tissue.

The present implants can be made by the same methods used to make implants now used in surgical reconstruction. For example, a form or mandrel in the shape of the desired implant can be made and then dipped in a solution or emulsion of the uncured polyphosphazene elastomer composition including conventional components such as fillers, plasticizers, pigments, processing aids and curing agents. Suitable solvents that can be used in dip coating include aromatic hydrocarbons such as toluene; cycloaliphatic hydrocarbons such as cyclohexane; ketones such as acetone or methylethyl ketone; ethers such as tetrahydrofuran, dimethoxyethane, dioxane, dimethylether of diethylene glycol alcohols such as methanol, fluorohydrocarbons such as freon.

Suitable fillers include silica, alumina, silica-alumina, hydrated alumina, magnesia, siloxane treated alumina and/or silica and the like.

Curing agents include free radical generating compounds such as peroxides (e.g. tert-butylperbenzoate) and azo compounds (e.g. azoisobutyrylnitrile).

Plasticizers include any oily material that is compatible with the polyphosphazene composition and will not cause an adverse tissue reaction. One such plasticizer is a low molecular weight fluoroalkoxy-substituted phosphazene oligomer containing about

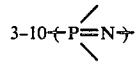

units in which the substituents on phosphorus comprise a mixture of two or more different fluoroalkoxy groups of the formula:

$$-O-(CH_2)_n-(CF_2)_mX \quad (I)$$

wherein n is an integer from 1 to 3, m is an integer from 1 to 10 and X is hydrogen or fluorine.

Multiple dips into the polyphosphazene solution or emulsion with drying stages in between dips can be used to obtain the desired film thickness. A thickness ranging from about 2–20 mils will usually give the required combination of suppleness and impermeability.

After the desired film thickness is built up the coated mandrel is heated to activate the curing agent. The required curing temperature will vary depending upon what curing agent is used but is generally in the range of about 100°–200° C. After completion of the cure, the sac is removed from the mandrel and the opening through which the mandrel was removed is sealed with a suitable adhesive or preferably with a patch of the same polyphosphazene film. The sac may be filled with the inert liquid (e.g. silicone gel or oil) using a hypodermic syringe or the sac may be constructed to include a fill valve or tube by methods well known in the prior art and not part of this invention.

The polyphosphazene elastomer used to make the implant sac are high molecular weight substantially linear polymers containing about 100 to 5,000

units wherein the substituents on phosphorus can be any of a broad range of substituent groups including alkoxy, substituted alkoxy (e.g. halo, nitro, alkoxy, aryl, aryloxy, amino, alkylamino, dialkylamino, and the like), aryl, substituted aryl (e.g. alkyl, alkoxy, aryl, aryloxy, halo, nitro, amino, alkylamino, dialkylamino, acyl, acyloxy, alkenyl, and the like), alkenyl, substituted alkenyl (e.g. halo, nitro, alkoxy, aryl, aryloxy, amino, alkylamino, dialkylamino, and the like), alkyl, aryl and up to about 5 mole percent halogen (e.g. chloro).

In one preferred embodiment the substituent groups are a mixture of aryloxy and substituted aryloxy groups. For example, a very useful membrane can be made from a high molecular weight substantially linear polyaryloxy phosphazene in which the substituent groups are a mixture of phenoxy and alkyl phenoxy groups. Of these, the more preferred polymers contain a mixture of about 30–60 mole percent phenoxy groups and about 40–70 mole percent p-ethylphenoxy groups.

In a more preferred embodiment at least a portion of the substituent groups (e.g. at least 10 mole percent) are fluoroalkoxy groups. Examples of these are 2-fluoroethoxy, 2,2-difluoroethoxy, 2,2,2-trifluoroethoxy, 3,3,3-trifluoro-n-propoxy, 2,3,3,3-tetrafluoropropoxy, 2,2,3,3-tetrafluoropropoxy, di-(trifluoromethyl)methoxy and the like. A highly preferred class of fluoroalkoxy groups can be represented by the formula:

$$-O-(CH_2)_n-(CF_2)_mX \quad (II)$$

wherein n is an integer from 1 to 3, m is an integer from 1 to 10 and X is hydrogen or fluorine.

In a still more preferred embodiment at least 50 mole percent of the substituent groups on phosphorus are fluoroalkoxy groups of formula II. The remaining groups may be any of the previously listed groups such as alkoxy, substituted alkoxy, aryloxy, substituted aryloxy, alkenoxy and the like. When over 75 mole percent of the groups are fluoroalkoxy groups, it is preferred that they be a mixture of at least two different fluoroalkoxy groups to improve flex characteristics of the sac.

In a most preferred embodiment the substituent groups are a mixture of trifluoroethoxy groups and one or more groups having the structure:

$$-O-(CH_2)_n-(CF_2)_pX \quad (III)$$

wherein n is an integer from 1 to 3, p is an integer from 2 to 7 and X is hydrogen or fluorine. A highly silicone-impermeable membrane can be obtained from a high molecular weight substantially linear polyphosphazene having about 10–70 mole percent trifluoroethoxy substituents and the balance a mixture of:

$$-O-CH_2-(CF_2)_pH \quad (IV)$$

and a small amount, up to about 10 mole percent, of o-allylphenoxy groups to impart curing properties to the elastomer.

The polyphosphazene elastomers are formulated with other conventional components (e.g. fillers, plasticizers, processing aids, pigments, curing agents, stabilizers, etc.) while in an uncured state—that is, without excessive cross-linking. Preferably a portion of the substituent groups (e.g. about 1–10 mole percent) are groups capable of chemical reaction to cross-link the polyphosphazene polymer and thus result in a cured or vulcanized elastomer. Such reactive groups usually have olefinic unsaturation although an alkyl group on an aryloxy substituent can react to cross-link under the influence of a peroxide catalyst. Typical cross-linking groups are alkenoxy (e.g. allyloxy) and alkenylaryloxy groups (e.g. o-allylphenoxy).

Tests were conducted to measure the permeability of a preferred film of the invention to a silicone fluid representative of fluids present in commercial breast implants. The first test film was prepared by mixing the following components in a Waring blender:

| Silica | 4 |
|---|---|
| Methanol | 56 |
| Polyphosphazene[1] | 20 |
| Varox DBPH[2] | 0.1 |

[1] A high molecular weight fluoroalkoxy-substituted polyphosphazene containing approximately 0.5 mole percent o-allylphenol groups
[2] R. T. Vanderbilt Company, Inc. brand 2,5-dimethyl, 2,5-di-t-butylperoxy hexane.

A 5 mil film was made from the above emulsion by applying several coatings to a glass panel and evaporating the methanol between coatings. The film was cured by heating at 160° C. for 20 minutes. Permeability of the film was tested by forming a depression in the film by squeezing it between two concentric Viton O-rings and filling the depression with a trimethylsiloxane-terminated polysiloxane oil. Two different viscosity oils were used; 100 cs and 1,000 cs. Two specimens were filled with each oil. The specimens were placed on filter paper and observations were made for bleed-through several times over a period of 47 days. No evidence of bleed-through was observed.

In view of these very encouraging results, further tests were conducted under more severe conditions and in a manner to directly compare the polyphosphazene membranes with a silicone rubber membrane of the type actually used in breast implants. Initially an elastomer composition was blended in a Brabender mixer as follows:

| | Blend | | |
|---|---|---|---|
| | A | B | C |
| Polyphosphazene[1] | 90 | 45 | 90 |
| Silastic HA-2[2] | 5.4 | 4.5 | 5.4 |
| Tullanox 500[3] | 27 | 4.5 | 18 |
| Elastomag 170[4] | 5.4 | 0 | 0 |

[1] Same type as previous fluoroalkoxy-substituted polyphosphazene
[2] Dow Corning brand silicone fluids on silica filler
[3] Tulco Inc. brand trimethylsiloxy surface treated fumed silica
[4] Morton brand MgO The compositions were blended at 65° C. and then removed from the blender and run through the nip of a two-roll mill. Curing agent (Varox DBPH 50 R. T. Vanderbilt Company, Inc. brand 50% 2,5-dimethyl, 2,5-di-t-butylperoxy hexane on an inert mineral carrier) was blended into each sample on the two-roll mill; 0.36 grams into sample A, 0.45 grams into sample B and 0.49 grams in sample C.

Nine films were made by compression molding each of the above blends in triplicate in a mold 5-inches diameter by 5 mils thick at 340° F. for 30 minutes. Gel permeability of two specimens of each film to a 1,000 centipoise silicone fluid was measured in a standard test and directly compared to the permeability of two commercial silica-filled silicone polymers. The elastomer specimens were held in a specially designed chamber in which they separated the 1,000 centipoise silicone fluid from a pre-weighed disc of filter paper. The silicone fluid was pressurized to 70 KPa causing the elastomer to be pressed into intimate contact with the filter paper. After 30 days under tests the filter paper was removed and re-weighed. A control disc of filter paper pressed into intimate contact with the elastomer by a 5 Kg weight was also re-weighed. The weight change of the control was subtracted from the weight change of the test specimen and the net change in weight was attributed to silicone oils passing through the specimen and being absorbed into the filter paper. The test results are given in the following table.

| Test Film | Thickness[1] (mm) | Permeability (ug/cm$^2$/24 hr) |
|---|---|---|
| A | 0.21 | <0.4[4] |
| B | 0.22 | <0.4 |
| C | 0.20 | <0.4 |
| X[2] | 0.22 | 74 ± 6[5] |
| Y[3] | 0.22 | 16 ± 2 |

[1] average of two specimens
[2] silica-filled polydimethylsiloxane
[3] silica-filled polydimethyldiphenylsiloxane
[4] below detection limit
[5] standard deviation The above results clearly demonstrate that polyfluoroalkoxyphosphazenes are impermeable to silicone fluids and will serve to form an effective barrier to prevent silicone fluids from migrating from a body implant into the surrounding tissue.

Although the main purpose of the invention is to provide a silicone-impermeable breast implant, the invention is not so limited and can be used to provide all forms of implants used in reconstructive plastic surgery.

We claim:

1. An article of manufacture suitable for use as a body implant, said article comprising a supple liquid-impermeable sac defining a cavity, said cavity containing an inert stable liquid, said sac comprising a continuous film of a cured polyphosphazene elastomer composition.

2. An article of claim 1 wherein said polyphosphazene elastomer is a fluoroalkoxy-substituted polyphosphazene elastomer.

3. An article of claim 2 wherein said stable liquid comprises a polysiloxane oil, a polysiloxane gel or a mixture of both.

4. An article of claim 3 wherein said polyphosphazene composition comprises a blend of a fluoroalkoxy-substituted polyphosphazene and a filler.

5. An article of claim 3 wherein said fluoroalkoxy-substituted polyphosphazene is a cured polyphosphazene wherein the substituent groups comprise mainly a mixture of two or more different fluoroalkoxy groups having the structure —O—$(CH_2)_n$—$(CF_2)_m$—X wherein n is an integer from 1 to 3, m is an integer from 1 to 10 and X is hydrogen or fluorine.

6. An article of claim 5 wherein said substituent groups prior to cure include groups capable of chemical reaction to cross-link said fluoroalkoxy-substituted polyphosphazene.

7. An article of claim 6 wherein said groups capable of chemical reaction to cross-link are groups which contain olefinic unsaturation.

8. An article of claim 7 wherein said groups which contain olefinic unsaturation are selected from alkenoxy groups and alkenylaryloxy groups.

9. An article of claim 8 wherein said groups are allyloxy groups.

10. An article of claim 8 wherein said groups are o-allylphenoxy groups.

11. An article of claim 5 wherein said mixture of fluoroalkoxy groups comprises a mixture of trifluoroethoxy groups and one or more groups having the structure $-O-(CH_2)_n-(CF_2)_pX$ wherein n is an integer having an average value of 1–3 and p is an integer having an average value of 2–7 and X is hydrogen or fluorine.

12. An article of claim 11 wherein said substituent groups prior to cure include groups capable of chemical reaction to cross-link said fluoroalkoxy-substituted polyphosphazene.

13. An article of claim 12 wherein said groups capable of chemical reaction to cross-link are groups which contain olefinic unsaturation.

14. An article of claim 13 wherein said groups which contain olefinic unsaturation are selected from alkenoxy groups and alkenylaryloxy groups.

15. An article of claim 14 wherein said groups are allyloxy groups.

16. An article of claim 14 wherein said groups are o-allylphenoxy groups.

17. An article of claim 3 wherein at least 10 mole percent of the substituent groups bonded to phosphorus are fluoroalkoxy groups and any remaining phosphorus substituent groups are selected from alkoxy, substituted alkoxy and up to 5 mole percent chloro groups.

18. An article of claim 1 wherein said polyphosphazene elastomer composition comprises a blend of a polyphosphazene and a polysiloxane.

19. An article of claim 18 wherein said polyphosphazene is a fluoroalkoxy-substituted polyphosphazene and said polysiloxane comprises dimethylsiloxane units, methylvinylsiloxane units, diphenylsiloxane units and/or methylphenylsiloxane units or mixtures of two or more of such siloxane units.

20. An article of claim 19 wherein said fluoroalkoxy-substituted polyphosphazene is substituted with a mixture of two or more different fluoroalkoxy groups having the structure $-O-(CH_2)_n-(CF_2)_m-X$ wherein n is an integer from 1 to 3, m is an integer from 1 to 10 and X is hydrogen or fluorine.

21. An article of claim 20 wherein said fluoroalkoxy-substituted polyphosphazene contains, prior to cure, about 1–15 mole percent o-allylphenoxy groups.

22. A prosthesis for subcutaneous implantation in a patient having need for such implantation, said prosthesis comprising a leak-proof flexible sac containing a polysiloxane gel or oil, said sac comprising a continuous cured poly-fluoroalkoxy-substituted phosphazene elastomer wall which is substantially impermeable to said polysiloxane gel or oil.

23. A prosthesis of claim 22 wherein said poly-fluoroalkoxy-substituted phosphazene elastomer contains two or more different fluoroalkoxy substituents having the structure $-O-(CH_2)_n-(CF_2)_m-X$ wherein n is an integer from 1 to 3, m is an integer from 1 to 10 and X is hydrogen or fluorine.

24. A prosthesis of claim 23 wherein said poly-fluoroalkoxy-substituted phosphazene is also substituted prior to cure with up to 15 mole percent of olefinically-unsaturated cross-linking groups.

25. A prosthesis of claim 24 wherein said cross-linking groups are o-allylphenoxy groups.

26. A prosthesis of claim 22 wherein said sac comprises a wall which comprises at least two continuous layers of flexible elastomer film, at least one of said layers comprising a cured poly-fluoroalkoxy-substituted phosphazene elastomer and at least one of said layers comprises a polysiloxane elastomer.

27. A prosthesis of claim 26 wherein said wall is a two-layer wall, the inner layer in contact with said silicone gel comprising a cured poly-fluoroalkoxy-substituted phosphazene elastomer and the outer layer comprising a cured polysiloxane elastomer.

28. An article of manufacture suitable for use as a liquid impermeable sac useful as a body implant for containing an inert stable liquid said article comprising a continuous membrane in the shape of said body implant forming a cavity, said membrane comprising a cured polyphosphazene elastomer composition.

29. An article of claim 28 wherein said polyphosphazene elastomer is a fluoroalkoxy-substituted polyphosphazene elastomer.

30. An article of claim 29 wherein said polyphosphazene composition comprises a blend of a fluoroalkoxy-substituted polyphosphazene and a filler.

31. An article of claim 29 wherein said fluoroalkoxy-substituted polyphosphazene is a cured polyphosphazene wherein the substituent groups comprise mainly a mixture of two or more different fluoroalkoxy groups having the structure $-O-(CH_2)_n-(CF_2)_m-X$ wherein n is an integer from 1 to 3, m is an integer from 1 to 10 and X is hydrogen or fluorine.

32. An article of claim 31 wherein said substituent groups prior to cure include groups capable of chemical reaction to cross-link said fluoroalkoxy-substituted polyphosphazene.

33. An article of claim 32 wherein said substituent groups capable of chemical reaction to cross-link said fluoroalkoxy-substituted polyphosphazene are o-allylphenoxy groups.

34. An article of claim 33 including means for admitting an inert stable liquid into said cavity to form said body implant.

* * * * *